(12) United States Patent
Steinberg et al.

(10) Patent No.: US 11,147,780 B2
(45) Date of Patent: Oct. 19, 2021

(54) MULTIDRUG PAIN MANAGEMENT PACKAGE

(71) Applicant: ALGIA PHARMA, LLC, Boca Raton, FL (US)

(72) Inventors: David L. Steinberg, Boca Raton, FL (US); Joseph Loskove, Boca Raton, FL (US); Hannah Thompson, Boca Raton, FL (US)

(73) Assignee: ALGIA PHARMA, LLC, Boca Raton, FL (US)

( * ) Notice: Subject to any disclaimer, the term of this patent is extended or adjusted under 35 U.S.C. 154(b) by 0 days.

(21) Appl. No.: 16/899,465

(22) Filed: Jun. 11, 2020

(65) Prior Publication Data
US 2021/0259999 A1 Aug. 26, 2021

Related U.S. Application Data

(60) Provisional application No. 62/980,935, filed on Feb. 24, 2020.

(51) Int. Cl.
| | | |
|---|---|---|
| *A61K 31/167* | (2006.01) | |
| *A61K 31/195* | (2006.01) | |
| *A61M 15/00* | (2006.01) | |
| *A61J 1/03* | (2006.01) | |
| *A61K 45/06* | (2006.01) | |

(52) U.S. Cl.
CPC ............ *A61K 31/167* (2013.01); *A61J 1/035* (2013.01); *A61K 31/195* (2013.01); *A61M 15/0003* (2014.02); *A61M 15/0048* (2014.02); *A61K 45/06* (2013.01)

(58) Field of Classification Search
CPC .... A61K 31/167; A61K 11/195; A61K 45/06; A61M 15/0003; A61J 1/035
See application file for complete search history.

(56) References Cited

U.S. PATENT DOCUMENTS

| | | | |
|---|---|---|---|
| 6,593,368 B2 * | 7/2003 | Magnus-Miller | .... A61K 31/415 514/561 |
| 9,390,457 B2 | 7/2016 | Baym et al. | |
| 2009/0264530 A1 | 10/2009 | Nickell | |
| 2013/0085171 A1* | 4/2013 | Ray, II | ..... A61P 21/02 514/401 |
| 2014/0322683 A1 | 10/2014 | Baym et al. | |
| 2015/0001124 A1 | 1/2015 | Yamashita et al. | |
| 2015/0174004 A1 | 6/2015 | Miyamoto et al. | |
| 2016/0147976 A1 | 5/2016 | Jain et al. | |
| 2019/0240430 A1 | 8/2019 | Jackson et al. | |
| 2019/0350883 A1* | 11/2019 | Chau | ........ A61K 9/48 |
| 2019/0365678 A1 | 12/2019 | Flanzraich et al. | |

FOREIGN PATENT DOCUMENTS

| | | |
|---|---|---|
| EP | 0759744 A1 | 5/1997 |
| GB | 1094594 A | 12/1967 |
| JP | 3117622 U | 1/2006 |
| WO | 2013/033033 A1 | 7/2013 |
| WO | WO 2015004505 * | 1/2015 |
| WO | 2019/067768 A2 | 4/2019 |
| WO | WO 2019/067768 A2 | 4/2019 |

OTHER PUBLICATIONS

Sulman Rafiq et al., "Multimodal analgesia versus traditional opiate based analgesia after cardiac surgery, a randomized controlled trial," Journal of Cardiothoracic Surgery, 2014, vol. 9, No. 52, pp. 1-8.
Delara Brandal et al., "Impact of Enhanced Recovery After Surgery and Opioid-Free Anesthesia on Opioid Prescriptions at Discharge From the Hospital: A Historical-Prospective Study," Anesthesia & Analgesia, Nov. 2017, vol. 125, No. 5, pp. 1784-1792.
Eric S. Schwenk, et al. "Multimodal Analgesia: The Foundation of a Successful Perioperative Experience," Anesthesiology New Special Edition, AnesthesiologyNews.com, 2019, pp. 17-23.
Meghan Lane-Fall, "APSF Highlights 12 Perioperative Patient Safety Priorities," The Official Journal of the Anesthesia Patient Safety Foundation, Oct. 2018, vol. 33, No. 2, pp. 33-68.
H. Shanthanna et al., "Caring for patients with pain during the COVID-19 pandemic: consensus recommendations from an international expert panel", Anaesthesia, 2020, pp. 1-10.
"FDA Innovation Challenge: Devices to Prevent and Treat Opioid Use Disorder", Jul. 9, 2019, retrieved from: http://www.fda.gov/about-fda/cdrh-innovation/fda-innovation-challenge-devices-prevent-and-treat-opioid-use-disorder.
U.S. Department of Health and Human Services, "Pain Management Best Practice Inter-Agency Task Force Report Updates, Gaps, Inconsistencies, and Recommendations," May 2019, retrieved from: https://www.hhs.gov/ash/advisory-committees/pain/reports/index.html.
Andrew D. Wiese et al., "The use of prescribd opioid analgesics & the risk of serious infections," Future Microbiology, 2018, vol. 13, No. 8, pp. 849-852.
Michael Eggerstedt et al., "Association of Perioperative Opioid-Sparing Multimodal Analgesia With Narcotic Use and Pain Control After Head and Neck Free Flap Reconstruction," JAMA Facial Plast Surg., 2019, vol. 21, No. 5, pp. 446-451.

(Continued)

*Primary Examiner* — Shirley V Gembeh
(74) *Attorney, Agent, or Firm* — Squire Patton Boggs (US) LLP

(57) ABSTRACT

Disclosed herein is a multidrug pain management package to dispense two or more medicaments to treat pain comprising a primary n-polygon, and one or more concentric m-polygons, wherein each side of the n-polygon and m-polygons have at least n or m-medicament chambers capable of holding the two or more medicaments. Also disclosed herein is a multidrug pain management package comprising a disk, wherein the disk is divided into equally spaced regions, and wherein each region has chambers capable of holding medicaments. Also disclosed herein are single formulations to treat pain.

20 Claims, 3 Drawing Sheets

(56) References Cited

OTHER PUBLICATIONS

Elizabeth C. Wick et al., "Postoperative Multimodal Analgesia Pain Management With Nonopioid Analgesics and Techniques: A Review", JAMA Surgery, May 2017, pp. E1-E7.
Erin E. Krebs et al., "Effect of Opioid vs Nonopioid Medications on Pain-Related Function in Patients with Chronic Back Pain or Hip or Knee Osteoarthritis Pain," JAMA, Mar. 6, 2018, vol. 319, No. 9, pp. 872-882.
Oleg Militsakh et al., "Development of Multimodal Analgesia Pathways in Outpatient Thyroid and Parathyroid Surgery and Association With Postoperative Opioid Prescription Patterns," JAMA Otolaryngology—Head & Neck Surgery, Nov. 2018, vol. 144, No. 11, pp. 1023-1029.
Michael Von Korff et al., "Assessing Global Pain Severity by Self-Report in Clinical and Health Services Research," Spine, 2000, vol. 25, No. 24, pp. 3140-3151.
Man David Kaye et al., "Multimodal analgesia as an essential part of enhanced recovery protocols in the ambulatory settings," Journal of Anaesthesiology Clinical Pharmacology, Apr. 2019, vol. 35 Suppl. 1, pp. S40-S45.
American Society of Anesthesiologists, "Multimodal Approach to Pain Management Reduces Opioid Use, Prescriptions After Joint Replacement," Mar. 1, 2018, pp. 1-2.
Thema Nicholson et al., "Multimodal Pain Management Protocol Versus Patient Controlled Narcotic Analgesia for Postoperative Pain Control after Shoulder Arthroplasty," The Archives of Bone and Joint Surgery, May 2018, vol. 6, No. 3, pp. 196-202.
Nanna B. Finnerup, "Nonnarcotic Methods of Pain Management," The New England Journal of Medicine, Jun. 2019, vol. 380, No. 25, pp. 2440-2448.
Kunal Karamchandani et al., "New Persistent Opioid Use After Surgery," American Society of Anesthesiologists, Feb. 2020, vol. 84, No. 2, pp. 8-10.
Steven L. Shafer, "Opioids. Opioids!! Opioids???," American Society of Anesthesiologists, Feb. 2020, vol. 84, No. 2, pp. 4-5.
Gary R. Haynes et al., "Anesthesiology and Pharmacy: A Road Toward Safety," American Society of Anesthesiologists, Feb. 2020, vol. 84, No. 2, pp. 16-19.
Code of Federal Regulations, Title 21, Chapter 2, Part 1300, Mar. 31, 2010, retrieved from: https://www.deadiversion.usdoj.gov/21cfr/cfr/21 00cfrt.htm.
Simon Haroutounian, "Postoperative opioids, endocrine changes, and immunosuppression," PAIN Reports, 2018, vol. 3, e640, pp. 1-5.
Toby K. Eisenstein et al., "The Role of Opioid Receptors in Immune System Function," Frontiers in Immunology, Dec. 2019, vol. 10, Article 2904, pp. 1-20.
Xuan Liang et al., "Opioid System Modulates the Immune Function: A Review," Translational Perioperative and Pain Medicine, 2016, vol. 1, No. 1, pp. 5-13.
Carlos A. Pino et al., "Prescription of opioids for acute pain in opioid naive patients," UpToDate, 2020, pp. 1-22.
MediPENSE, "Blister Packaging is Best for Solid Medication Dispensing and Adherence," 2019, pp. 1-12.
Vivek Mehta et al., "Acute Pain Management in Opioid Dependent Patients," Reviews in Pain, Oct. 2009, vol. 3, No. 2, pp. 10-14.
South Dakota State Medical Association, "Effective Management of Acute Pain: Recommendations from the Ad Hoc Committee on Pain Management and Prescription Drug Abuse," Jun. 2019, pp. 1-31.
Frances Wood et al., "Process evaluation of the impact and acceptability of a polypill for prevention of cardiovascular disease," BMJ Open, 2015, vol. 5, e008018, pp. 1-9.
International Search Report and Written Opinion dated Apr. 27, 2021 for International Application No. PCT/US2021/019283, 14 pages.
Catty Corporation "Choosing the Right Aluminum Foil," Apr. 15, 2017; retrieved Mar. 28, 2021; https://cattycorp.com/2017/04/15/choosing-right-aluminum-foil/>.entire document; 3 pages.

\* cited by examiner

MULTIDRUG PAIN MANAGEMENT PACKAGE

This application claims priority to U.S. application 62/980,935 filed on Feb. 24, 2020.

FIELD

Provided herein are packages to hold and dispense medicaments for the treatment of pain. Also provided herein, are formulations for treating pain.

BACKGROUND

Due to the inadequate methods of organized, evidence-based pain treatment, and pain control, medical providers rely on doling out single types of narcotic based pain pills. As a patient experiences increases in pain, historically medical providers' first line and primary treatment plan is to increase the number of narcotic pills ingested, resulting in opioid addiction. Although this temporarily treats pain symptoms, the long term effects of narcotics on brain chemistry has unfortunately led to a worldwide opioid epidemic.

The Food and Drug Administration ("FDA") has identified the opioid epidemic as one of the most profound public health crises facing the United States and suggested that the current crisis of opioid overdose deaths requires innovative approaches. FDA Innovation Challenge: Devices to Prevent and Treat Opioid Use Disorder, Jul. 9, 2019. The FDA estimates that in 2007, more than 33 million Americans misused opioids, an increase from 29 million five years earlier. Further, the FDA estimates that since 2000, more than 300,000 Americans have died of an opioid overdose, its preliminary data for 2016 indicate at least 64,000 drug overdose deaths attributable to opioid overdoses. While the U.S. government plans to address the epidemic through education and monitoring programs, such strategies may not sufficiently address the core of the problem, which is the addictive nature of the underlying opioid compounds and routine by which physicians worldwide utilize and depend on opioids as first line therapy for acute pain.

It is also well-known that opioid drug use and exposure induces immunosuppression via various biological mechanisms. Narcotic use downregulates acquired and innate immune pathways. For example, morphine has been linked to the disruption of natural killer cells and the decreased production of immune modulator cell production. As a result, long term narcotic use increases incidence of infection by suppressing the body's ability to launch an effective immune response. Studies consistently report that patients who utilized long acting and high potency opioid formulations, high dose opioids, and opioids previously described as exhibiting immunosuppressive properties (i.e., morphine, codeine, fentanyl and methadone) had the highest risk for infection. (Liang, X. et al. (2016); Haroutounian, S. (2018); Eisenstein, T. K., et al. (2019))

Patients infected with COVID-19 are highly susceptibility to secondary infection due to their hyper-inflammatory state. Significant immune system changes occur in patients with COVID-19. This includes a higher risk of mortality observed in the elderly alongside individuals who have hypertension; diabetes; coronary artery disease; and chronic lung disease which can lead to SARS (severe acute respiratory syndrome).

COVID-19 patients can suffer from severe respiratory symptoms, including respiratory depression, which can be exacerbated by opioid usage. COVID-19 affects many people who must be admitted to the hospital. Patients who have been placed on a ventilator or respirator for any period of time as a result of COVID-19 have pain throughout their mouth and throat as a result of intubation. In addition, patients who need to undergo emergent surgeries or procedures are affected. For example, these patients include patients who give birth vaginally or via Cesarean section, patients who require emergency surgeries, or patients who require urgent cancer removal procedures.

Challenge arises when choosing a pain control plan to limit or prevent an immunosuppression cascade. Ingesting opioids for pain control can create serious adverse effects with the potential to further suppress an already taxed immune system. Furthermore, immune cells and their by-products have a role in both inflammatory and neuropathic pain pathways, which can directly affect how quickly a patient recovers from an initial pain insult. With a concomitant COVID-19 infection, these patients need to limit opioid exposure in order to optimize immune system responsiveness.

Combining various types of non-narcotic pain therapies can effectively treat pain as effectively as a narcotic or opiates, without the potential for addiction and common side effects that come with narcotics and narcotic withdrawal (i.e. chills, shaking, constipation, elevated temperature). Further, non-narcotic pain therapies can limit the effectiveness of the immune system of the immune system. By using an opioid sparing medication regimen that combines treating multiple pathways simultaneously that are responsible for generating the pain response, a patient maintains control without fear of addiction, while concomitantly providing an effective and addiction free pain regimen.

Aspects of non-narcotic pain therapies have proven to be effective in post-operative in-patient hospital settings. Post-operative patients often have the most acute types of pain associated with surgery and will complain of higher degrees of pain than a patient who has not undergone surgery.

For post-discharge use by patients, such non-narcotic pain therapies require patients to navigate complex prescriber prescriptions, a complex schedule for such drug and patient discretion with following instructions for such complex prescriptions, especially when dosses are mixed.

In order to address these concerns, a package is disclosed that includes pain formulations stored in a unique package that accounts for the prescribed dosage. This apparatus, hereinafter referred to as a multidrug pain management dispenser, guides clinicians who are unsure about how to adequately address pain management without providing narcotics. The multidrug pain management package provides patients with a long-needed solution to treating pain in a narcotic free environment. The multidrug pain management package allows a patient to self-administer the pain formulations once prescribed while tapering the medication dosages to eventually reduce the need for pain medications.

SUMMARY

The present disclosure provides a package to dispense two or more medicaments to treat pain. The present disclosure also provides formulations for medicaments for use in a package to dispense two or more medicaments. This disclosure sets forth processes, in addition to making and using the same, and other solutions to problems in the relevant field.

In some aspects, there is provided a package to dispense two or more medicaments to treat pain comprising a primary n-polygon shaped blister layer, wherein each side of the n-polygon has at least n-medicament chambers capable of holding the two or more medicaments, and wherein the n-medicament chambers each comprise a blister layer forming a sealed chamber capable of holding the two or more medicaments, wherein the two or more medicaments are between the blister layer and the chamber holding the two or more medicaments; and one or more concentric m-polygons within the primary n-polygon wherein the first m-polygon has n−1 or fewer sides; wherein each additional, optional concentric m-polygon has m−1 or fewer sides from the previous concentric m-polygon, wherein each side of the m-polygon has at least m-medicament chambers capable of holding the two or more medicaments.

In some aspects, there is provided a package to dispense two or more medicaments to treat pain comprising a disk shaped blister layer, wherein the disk is divided into equally spaced regions, and wherein each region has at least o-medicament chambers capable of holding the two or more medicaments, and wherein the o-medicament chambers each comprise a blister layer forming a medicament chamber capable of holding the two or more medicaments, wherein the two or more medicaments are between the blister layer and the medicament canopy holding the two or more medicaments.

In some aspects, there is provided a single formulation comprising a single formulation comprising acetaminophen and one or more nonsteroidal anti-inflammatory drug.

In some aspects, there is provided a single formulation comprising acetaminophen; one or more nonsteroidal anti-inflammatory drug; a gabapentinoid and one or more additional active ingredients for use with an apparatus to dispense the medicaments to treat pain.

In some embodiments, there is provided an inhaler to dispense any of the formulations herein. In certain embodiments, there is provided an inhaler to dispense two or more medicaments to treat pain comprising a canister containing pressurized contents for dispersing a dose of two or more medicaments to a patient; a locking mechanism that prevents another dose during a set time period; and a mouthpiece, wherein the mouthpiece holds the canister, and wherein the mouthpiece allows dispersal of the medicaments to a patient from the canister. In certain embodiments, any conventional inhaler can be used.

In certain embodiments, the inhaler provides a dosage every 8 hours. In certain embodiments, the inhaler provides a dosage every 7 hours. In certain embodiments, the inhaler provides a dosage every 6 hours. In certain embodiments, the inhaler provides a dosage every 5 hours. In certain embodiments, the inhaler provides a dosage every 4 hours. In certain embodiments, the inhaler provides a dosage every 3 hours. In certain embodiments, the inhaler provides a dosage every 2 hours. In certain embodiments, the inhaler provides a dosage every 1 hour.

In some aspects, there is provided a method of treating pain, comprising administering two or more medicaments in a package, in a single formulation or in an inhaler to a subject in need thereof.

The following description is presented to enable one of ordinary skill to make and use the disclosed subject matter and to incorporate it in the context of applications. Various modifications, as well as a variety of uses in different applications, will be readily apparent to those skilled in the art, and the general principles defined herein may be applied to a wide range of embodiments. Thus, the present disclosure is not intended to be limited to the embodiments presented, but is to be accorded the widest scope consistent with the principles and novel features disclosed herein.

BRIEF DESCRIPTION OF THE FIGURES

FIG. 3 illustrates different views of a chamber to hold a medicament in an embodiment of a package to dispense two or more medicaments to treat pain.

DETAILED DESCRIPTION

Figure 1:
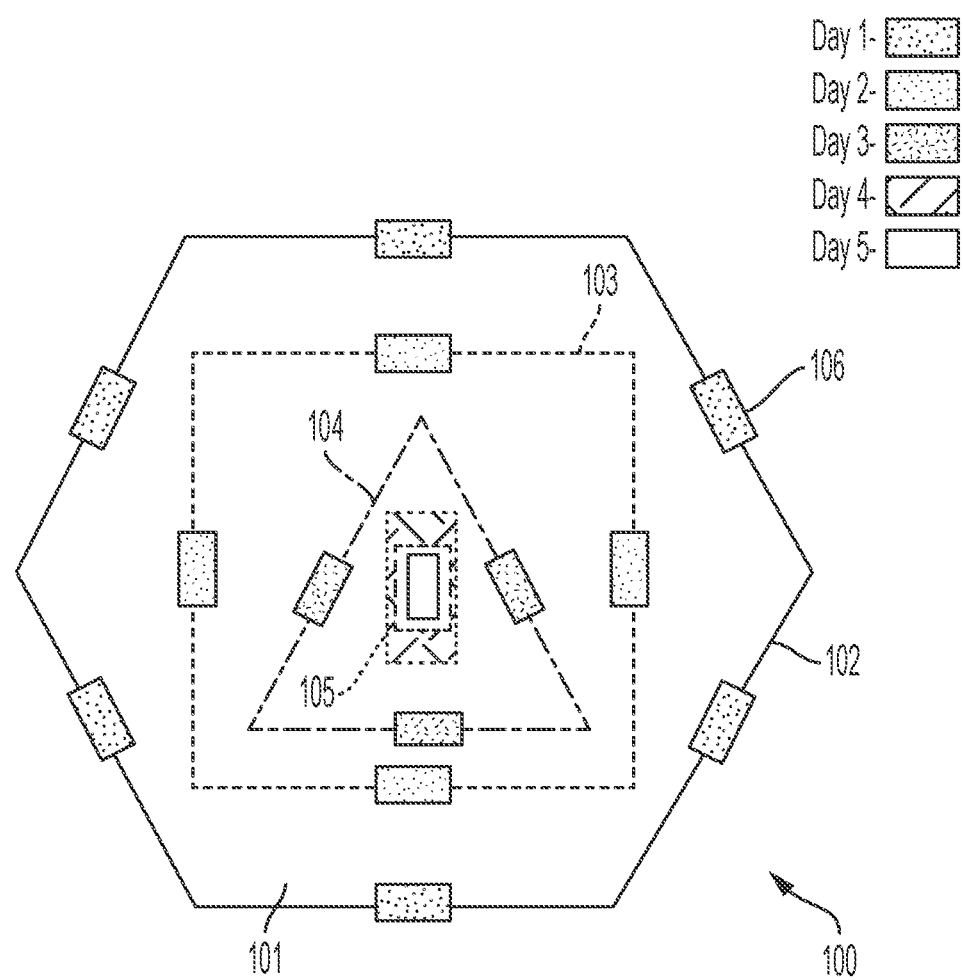
FIG. 1 is a schematic display of a top view of one embodiment of a package to dispense two or more medicaments to treat pain.

The following description is presented to enable one of ordinary skill to make and use the disclosed subject matter and to incorporate it in the context of applications. Various modifications, as well as a variety of uses in different applications, will be readily apparent to those skilled in the art, and the general principles defined herein may be applied to a wide range of embodiments. Thus, the present disclosure is not intended to be limited to the embodiments presented, but is to be accorded the widest scope consistent with the principles and novel features disclosed herein.

Definitions

When referring to the terms provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "narcotic," as used herein, unless otherwise specified, refer to drugs classified by the United States Food and Drug Administration. See Code of Federal Regulations, Title 21, Chapter 2, part 1300. In certain embodiments, the term "narcotic" refers to each of the opiates, including its isomers, esters, ethers, salts, and salts of isomers, esters, and ethers whenever the existence of such isomers, esters, ethers, and salts is possible within the specific chemical designation. See Id. at 1308.11(b), 1308.11 (c), and 1308.11 (d). In certain embodiments, the term "narcotic" refers to, but is not limited to: raw opium, opium extracts, opium fluid extracts, powdered opium, granulated opium, deodorized opium and tincture of opium, apomorphine, codeine, etorphine hydrochloride, ethylmorphine, hydrocodone, hydromorphone, metopon, morphine, oxycodone, oxymorphone, thebaine, mixed alkaloids of opium, cocaine, ecgonine, methamphetamine, amphetamine, phenmetrazine, and methylphenidate.

The term "pain," as used herein, unless otherwise specified, refers to the physical suffering resulting from illness, injury, or post-operative procedure to a patient. In certain embodiments, pain is caused by the use or dependency of a patient on opiates.

The term "polygon," as used herein, unless otherwise specified, refers to a geometric design with at least three straight sides and angles.

The term "line," as used herein, unless otherwise specified, refers to a connection between two points without curvature.

The term "concentric," as used herein, unless otherwise specified, refers to two or more polygons that share the same center of axis.

The term "about," as used herein unless otherwise specified, refers to a range of +/−10% the value of a number.

The term "quick response code" or "QR," as used herein, unless otherwise specified, refers to a type of barcode which can be read by a digital device and which stores information. A quick response code, also called a QR code, is most frequently used to track information about products. QR codes consist of black squares arranged in a grid (matrix) on a white background. QR code readers can extract data from the patterns that are present in the QR code matrix. QR codes are considered an advancement from older, two-dimensional barcodes.

The term "medical professional" as used herein, unless otherwise specified, refers to doctors, nurses, physician assistants, and pharmacists.

The term "patient" as used herein, unless otherwise specified, refers to an individual in need of treatment for pain. In certain embodiments, the term "patient" is synonymous with the term "subject."

Embodiments of Multidrug Pain Management Package

In some embodiment, provided herein is multidrug pain management package to dispense two or more medicaments to treat pain. FIG. 1 illustrates a diagram of an exemplary multidrug pain management package. The package 100, includes the following components: a blister layer 101 comprising a hexagon 102, a square 103, a triangle 104, and a line 105. Additionally, a chamber capable of holding two or more medicaments 106 are arranged on each side of the hexagon, square, triangle, and within the line.

Figure 2:
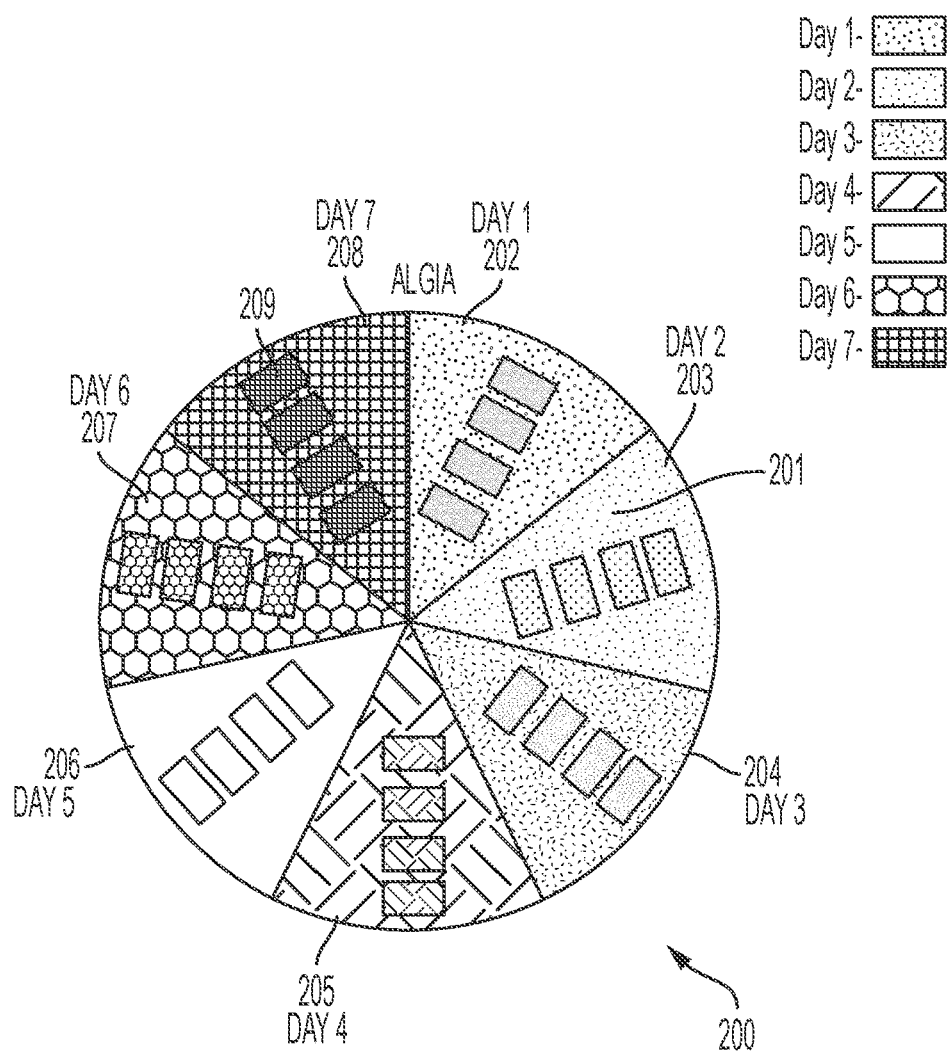
FIG. 2 is a schematic display of a top view of one embodiment of a package to dispense two or more medicaments to treat pain.

In an alternative embodiment, the multidrug pain management package is illustrated in FIG. 2. The multidrug pain management package 200, includes a blister layer 201 comprising a disk 202, that is divided into several equally spaced regions 202-208, with one or more medicament chambers 209 placed within each region.

Figure 3A:
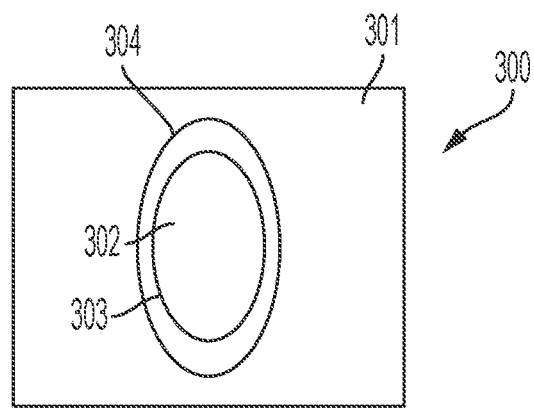
FIG. 3A is a top view.
Figure 3B:
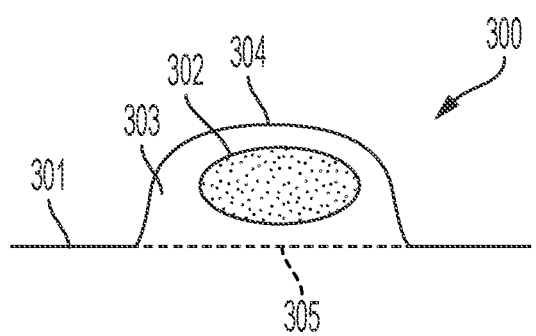
FIG. 3B is a cross-sectional view.
Figure 3C:
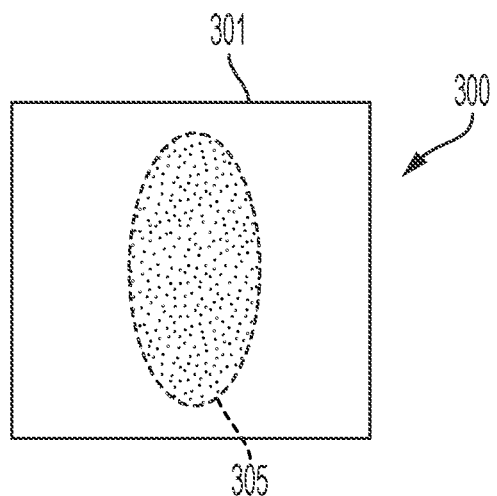
FIG. 3C is a bottom view.

In some embodiments, the multidrug pain management package 300 has a medicament chamber 303 as illustrated according to FIGS. 3A-3C. On one side of the blister layer 301, the medicament 302 is placed between the blister layer and medicament canopy 304. On the other side of the medicament chamber 303, the medicament is held in place by a rupturable layer 305.

In some embodiments, the multidrug pain management package comprises a blister layer. In certain embodiments, the blister layer comprises one or more medicament chambers, wherein each of the one or more medicament chambers are located on each side of a polygon. In certain embodiments, the blister layer comprises a rupturable layer on the bottom of each of the medicament chamber.

In certain embodiments, the material for the blister layer comprises a thermoplastic material. In certain embodiments the material for the blister layer comprises polyvinylchloride. In certain embodiments, the material for the blister layer comprises polyolefin. In certain embodiments, the material for the blister layer comprises cardboard.

In some embodiments, the blister layer's thickness is dependent on the medicament. In certain embodiments, the blister layer's thickness is thinner for smaller medicaments. In certain embodiments, the blister layer's thickness is thicker for larger medicaments. In some embodiments, the blister layer's thickness comprises at least 0.005 inches, at least 0.006 inches, at least 0.007 inches, at least 0.008 inches, at least 0.009 inches, at least 0.010 inches, at least 0.011 inches, at least 0.012 inches, at least 0.013 inches, at least 0.014 inches, and at least 0.015 inches.

In certain embodiments, the blister layer's thickness ranges from at least 0.005 inches to 0.015 inches. In certain embodiments, the blister layer's thickness ranges from at least 0.007 inches to 0.013 inches. In certain embodiments, the blister layer's thickness ranges from at least 0.019 inches to 0.011 inches.

In some embodiments, the multidrug pain management package comprises a primary n-sided polygon. In certain embodiments, the number of sides of the n-sided polygon comprises 8, 7, 6, 5, 4, or 3 sides.

In some embodiments, the multidrug pain management package comprises a series of one or more concentric m-polygons within the n-polygon. In some embodiments, the number of sides of the one or more m-polygons comprises 7, 6, 5, 4, or 3 sides. In some embodiments, the package comprises at least 2, at least 3, at least 4, at least 5, at least 6, or at least 7 m-concentric polygons within the n-polygon. In some embodiments, the package comprises 7 concentric m-polygons within the n-polygon. In some embodiments, the package comprises 6 concentric m-polygons within the n-polygon. In some embodiments, the package comprises 5 concentric m-polygons within the n-polygon. In some embodiments, the package comprises 4 concentric m-polygons within the n-polygon. In some embodiments, the package comprises 3 concentric m-polygons within the n-polygon. In some embodiments, the package comprises 2 concentric m-polygons within the n-polygon.

In some embodiments, the multidrug pain management package comprises a primary n-polygon which is a hexagon. In certain embodiments, the package comprises a first m-polygon which is a square or rectangle inside the hexagon. In certain embodiments, the package comprises a third concentric m-polygon which is a triangle inside the square or rectangle.

In certain embodiments, the blister layer of the multidrug pain management package comprises one or more n-polygons. In certain embodiments, the multidrug pain management package comprises a octagon. In certain embodiments, the multidrug pain management package comprises a heptagon. In certain embodiments, the multidrug pain management package comprises a hexagon. In certain embodiments, the multidrug pain management package comprises a pentagon. In certain embodiments, multidrug pain management package comprises a square. In certain embodiments, the multidrug pain management package comprises a rectangle. In certain embodiments, the multidrug pain management package comprises a triangle. In certain embodiments, the multidrug pain management package comprises a line.

In some embodiments, the multidrug pain management package comprises a primary n-polygon that is a hexagon, a concentric m-polygon within the hexagon that is a square or rectangle, and a line within the square, the line concentric with the square and hexagon.

In some embodiments, the multidrug pain management package comprises an n-polygon within a square or rectangular blister layer.

In some embodiments, the medicament chamber is sized to completely contain two or more medicaments.

In some embodiments, the blister layer comprises a rupturable layer that encloses the medicament canopy and holds the medicament in the canopy chamber. In certain embodiments, the canopy chamber is made of a transparent material. In certain embodiments, the rupturable layers hermetically seals the medicament chamber. In certain embodiments, the rupturable layer is ruptured by applying force from a patient allowing release of the medicaments from the medicament chamber through the rupturable layer and to the patient.

In some embodiments, the rupturable layer comprises a metal foil. In certain embodiments the rupturable layer comprises aluminium or an aluminium alloy. In some embodiments, the rupturable layer comprises a thermoplastic material. In certain embodiments the rupturable layer comprises polyvinylchloride. In certain embodiments, the rupturable layer comprises polyolefin. In certain embodiments, the rupturable layer comprises cardboard. In certain embodiments, the rupturable layer comprises an combination of any of the previous embodiments.

In some embodiments, the two or more medicaments comprise a single formulation. In some embodiments, the single formulation is a pill comprising two or more medicaments. In some embodiment, the single formulation is a capsule comprising two or more medicaments. In some embodiments, the single formulation is a gelcap comprising two or more medicaments. In some embodiments, the single formulation is a enteric coated capsule comprising two or more medicaments. In some embodiments, the single formulation is a liquid comprising two or more medicaments.

In some embodiments, the multidrug pain management package comprises a different color for each primary n-polygon, concentric m-polygon, and/or line.

In some embodiments, the multidrug pain management package comprises labels for each primary n-polygon, concentric m-polygon, and/or line. In certain embodiments, the labels for each n-polygon, concentric m-polygon, and/or line comprise the day for which each patient will use the medicament, in the n-polygon, concentric m-polygon, and/or line.

In some embodiments, a multidrug pain management package comprises a quick response code (QR code). In certain embodiments, the QR code is unique and allows tracking of individual packages. In certain embodiments, the QR code allow registration of the product with the manufacturing company by the patient to whom it was prescribed.

In some aspects, a method of manufacturing is presented for a package to dispense two or more medicaments to treat pain comprising a primary n-polygon shaped blister layer, wherein each side of the n-polygon has at least n-medicament chambers capable of holding the two or more medicaments, and wherein the n-medicament chambers each comprise a blister layer forming a sealed chamber capable of holding the two or more medicaments, wherein the two or more medicaments are between the blister layer and the chamber holding the two or more medicaments; and one or more concentric m-polygons within the primary n-polygon wherein the first m-polygon has n−1 or fewer sides; wherein each additional, optional concentric m-polygon has m−1 or fewer sides from the previous concentric m-polygon, wherein each side of the m-polygon has at least m-medicament chambers capable of holding the two or more medicaments.

In some aspects, a method of manufacturing is presented for a package to dispense two or more medicaments to treat pain comprising a disk shaped blister layer, wherein the disk is divided into equally spaced regions, and wherein each region has at least o-medicament chambers capable of holding the two or more medicaments, and wherein the o-medicament chambers each comprise a blister layer forming a medicament chamber capable of holding the two or more medicaments, wherein the two or more medicaments are between the blister layer and the medicament canopy holding the two or more medicaments.

In some aspects, the package is administered by the patient to manage pain post-discharge by a physician.

In some aspects, the package is administered to the patient to manage pain post-discharge by a physician.

In some aspects, the package is administered by the patient to manage pain associated with a COVID-19 infection.

In some aspects, the package is administered by the patient to manage pain, wherein the patient is also infected with COVID-19.

In some aspects, the package is administered to the patient to manage pain associated with a COVID-19 infection. In certain aspects, a medical professional administers the package to the patient to manage pain associated with a COVID-19 infection.

In some aspects, the package is administered to the patient to manage pain, wherein the patient is also infected with COVID-19. In certain aspects, a medical professional administers the package to the patient to manage pain, wherein the patient is also infected with COVID-19.

Pharmaceutical Compositions

In some aspects a single formulation comprises acetaminophen and one or more nonsteroidal anti-inflammatory drug (NSAID).

In aspects embodiments, a single formulation comprises acetaminophen, one or more nonsteroidal anti-inflammatory drug (NSAID), one or more gabapentinoid, and one or more additional active ingredients.

In some embodiments, the single formulation comprises about 450 mg of acetaminophen. In some embodiments, the single formulation comprises about 500 mg of acetaminophen. In some embodiments, the single formulation comprises about 550 mg of acetaminophen. In some embodiments, the single formulation comprises about 600 mg of acetaminophen. In some embodiments, the single formulation comprises about 650 mg of acetaminophen. In some embodiments, the single formulation comprises about 700 mg of acetaminophen. In some embodiments, the single formulation comprises about 750 mg of acetaminophen. In some embodiments, the single formulation comprises about 800 mg of acetaminophen. In some embodiments, the single formulation comprises about 850 mg of acetaminophen. In some embodiments, the single formulation comprises about 900 mg of acetaminophen. In some embodiments, the single formulation comprises about 950 mg of acetaminophen. In some embodiments, the single formulation comprises about 1000 mg of acetaminophen. In some embodiments, the single formulation comprises about 1050 mg of acetaminophen.

In some embodiments, the single formulation comprises acetaminophen ranging from about 30 mg to about 1050 mg. In some embodiments, the single formulation comprises acetaminophen ranging from about 50 mg to about 1000 mg. In some embodiments, the single formulation comprises acetaminophen ranging from about 100 mg to about 900 mg. In some embodiments, the single formulation comprises acetaminophen ranging from about 200 mg to about 800 mg. In some embodiments, the single formulation comprises acetaminophen ranging from about 300 mg to about 700 mg. In some embodiments, the single formulation comprises acetaminophen ranging from about 400 mg to about 600 mg.

In some embodiments, the single formulation comprises about 25 mg of a NSAID. In some embodiments, the single formulation comprises about 50 mg of a NSAID. In some embodiments, the single formulation comprises about 75 mg of a NSAID. In some embodiments, the single formulation comprises about 100 mg of a NSAID. In some embodiments, the single formulation comprises about 125 mg of a NSAID. In some embodiments, the single formulation comprises about 150 mg of a NSAID. In some embodiments, the single formulation comprises about 175 mg of a NSAID. In some embodiments, the single formulation comprises about 200 mg of COX-2 selective NSAID.

In some embodiments, the single formulation comprises an NSAID ranging from about 25 mg to about 200 mg. In some embodiments, the single formulation comprises an NSAID ranging from about 50 mg to about 150 mg. In some embodiments, the single formulation comprises an NSAID ranging from about 75 mg to about 100 mg.

In some embodiments, the NSAID is ibuprofen. In some embodiments, the NSAID is celecoxib. In some embodiments, the NSAID is meloxicam. In some embodiments, the NSAID is Celebrex. In some embodiments, the NSAID comprises a COX-2 selective NSAID.

In some embodiments, the NSAID is selected from among, but not limited to, Aspirin, Naproxen Sodium, Naproxen, Vimovo (Naproxen/Esomeprazole), Salsalate (Amigesic), Celecoxib (Celebrex), Diclofenac (Voltaren), Etodolac (Lodine), Ibuprofen (Motrin), Indomethacin (Indocin), Ketoprofen (Orudis), Ketorolac (Toradol), Nabumetone (Relafen), Naproxen (Aleve, Naprosyn), Oxaprozin (Daypro), Piroxicam (Feldene), Sulindac (Clinoril), and Tolmetin (Tolectin).

In some embodiments, the single formulation comprises about 25 mg of a gabapentinoid. In some embodiments, the single formulation comprises about 50 mg of a gabapentinoid. In some embodiments, the single formulation comprises about 75 mg of a gabapentinoid. In some embodiments, the single formulation comprises about 100 mg of a gabapentinoid. In some embodiments, the single formulation comprises about 125 mg of a gabapentinoid. In some embodiments, the single formulation comprises about 150 mg of a gabapentinoid. In some embodiments, the single formulation comprises about 175 mg of a gabapentinoid. In some embodiments, the single formulation comprises about 200 mg of a gabapentinoid.

In some embodiments, the single formulation comprises a gabapentinoid ranging from about 25 mg to about 200 mg. In some embodiments, the single formulation comprises a gabapentinoid ranging from about 50 mg to about 150 mg. In some embodiments, the single formulation comprises a gabapentinoid ranging from about 75 mg to about 100 mg.

In some embodiments, the gabapentinoid is (S)-3 isobutyl-γ aminobutyric acid. In some embodiments, the gabapentinoid is gabapentin.

In some embodiments, the gabapentinoid comprises, but is not limited to Gabapentin (Neurontin, Gabagamma), Gabapentin extended-release (Gralise), Enacarbil (Horizant), Mirogabalin (Tarlige), Phenibut (Anvifen, Fenibut, Noofen), Baclofen (Lioresal), and Pregabalin (Lyrica).

In some embodiments, the single formulation comprises 500 mg of acetaminophen, 50 mg of a nonsteroidal anti-inflammatory drug, 50 mg of gabapentinoid, and one or more active ingredients.

In some embodiments, the single formulation comprises 650 mg of acetaminophen, 100 mg of a nonsteroidal anti-inflammatory drug, 75 mg of a gabapentinoid, and one or more active ingredients.

In some embodiments, the single formulation comprises 1000 mg of acetaminophen, 200 mg of a nonsteroidal anti-inflammatory drug, 75 mg of gabapentinoid, and one or more active ingredients.

In some embodiments, the single formulation comprises 500 mg of acetaminophen, 50 mg of a nonsteroidal anti-inflammatory drug, 50 mg of a gabapentinoid, and one or more active ingredients.

In some embodiments, the single formulation comprises 650 mg of acetaminophen, 100 mg of a nonsteroidal anti-inflammatory drug, 75 mg of a gabapentinoid, and one or more active ingredients.

In some embodiments, the single formulation comprises 1000 mg of acetaminophen, 100 mg of a nonsteroidal anti-inflammatory drug, 75 mg of a gabapentinoid, and one or more active ingredients.

In some embodiments, the single formulation comprises 1000 mg of acetaminophen, 200 mg of a nonsteroidal anti-inflammatory drug, 75 mg of a gabapentinoid, and one or more active ingredients.

In some embodiments, the single formulation of any of the previous claims comprises a non-steroidal anti-inflammatory drug that is a COX-2 selective nonsteroidal anti-inflammatory drug.

In some embodiments, the single formulation of any of the previous claims comprises a gabapentinoid that is gabapentin.

In some embodiments, the active ingredients comprise vitamins and mood enhancers that boost the immune system, promote healing and general well-being. In certain embodiments, the vitamins comprise Vitamins A, B6, B12, C, D, E, K, biotin, niacin, folate, pantothenic acid, riboflavin, thiamine, choline, carnitine, and zinc. In certain embodiments, the mood enhancers comprise alpha-2 receptor agonists, H2 blockers, SSRIs (Selective Serotonin Reuptake Inhibitors), SNRIs (Serotonin Norepinephrine Reuptake Inhibitors), and TCAs (Tricyclic Antidepressants).

In some embodiments, the additional active ingredient comprises one or more of anti-convulsants or anti-seizure medications, alpha 2 agonists, corticosteroids, H2 blockers, proton pump inhibitors, antacids, SSRIs (Selective Serotonin Reuptake Inhibitors), SNRIs (Serotonin Norepinephrine Reuptake Inhibitors), TCAs (Tricyclic Antidepressants), muscle relaxants, sleep aids drugs, and sleep aids natural.

In some embodiments, the anticonvulsants or anti-seizure medications comprise, but not limited to, lamotrigine, levetiracetam, oxcarbazepine, phenytoin, phenobarbital, and topiramate.

In some embodiments, the alpha 2 agonists comprise, but not limited to, Clonidine, Clonidine patch, Methyldopa, Tizanidine, Guanfacine or Lofexidine.

In some embodiments, the corticosteroids comprise, but not limited to, prednisone, prednisolone, and dexamethasone.

In some embodiments, the H2 blockers comprise, but not limited to, famotidine, cimetidine, ranitidine, pepcid, and nizatidine.

In some embodiments, the Proton Pump Inhibitors comprise, but not limited to, Omeprazole (Prilosec, Prilosec OTC, and Zegerid), Lansoprazole (Prevacid), Pantoprazole (Protonix), Rabeprazole (Aciphex), Esomeprazole (Nexium), and Dexlansoprazole (Dexilant).

In some embodiments, the antacids comprise, but not limited to, Alka-Seltzer, Maalox, Mylanta, Rolaids, and Tums.

In some embodiments, the SSRIs (Selective Seratonin Reuptake Inhibitors) comprise, but not limited to, Citalopram (Celexa), Escitalopram (Lexapro), Fluoxetine (Prozac), Paroxetine (Paxil, Pexeva), and Sertraline (Zoloft).

In some embodiments, the SNRIs (Seratonin Norepinephrine Reuptake Inhibitors) comprise, but not limited to, Venlafasxine and Duloxetine.

In some embodiments, TCAs (Tricyclic Antidepressants) comprise, but not limited to, Amitriptyline, Amoxapine, Clomipramine, Desipramine, Doxepin, Imipramine, Nortriptyline and Protriptyline.

In some embodiments, muscle relaxants comprise, but not limited to, Soma, Flexeril, and Skelaxin.

In some embodiments, sleep aids comprise, but not limited to, Benzodiazepines, Non-benzodiazepine hypnotics, Antidepressants, Diphenhydramine, melatonin and Orexin receptor antagonists In some embodiments, the single formulation comprises acetaminophen, celecoxib, gabapentin, and famotidine according to the formulations of Table 1.

TABLE 1

| | Acetaminophen (mg) | Celecoxib (mg) | Gabapentin (mg) | Famotidine (mg) |
|---|---|---|---|---|
| 1 | 1000 | 133 | 200 | 5 |
| 2 | 1000 | 67 | 200 | 5 |
| 3 | 1000 | 67 | 150 | 5 |
| 4 | 750 | 67 | 100 | 5 |
| 5 | 750 | 50 | 100 | 5 |
| 6 | 500 | 50 | 50 | 5 |
| 7 | 500 | 33 | 0 | 5 |
| 8 | 500 | 25 | 0 | 5 |

In some embodiments, the single formulation comprises acetaminophen, celecoxib, gabapentin, famotidine, and decadron according to the formulations of Table 2.

TABLE 2

| | Acetaminophen (mg) | Celecoxib (mg) | Gabapentin (mg) | Famotidine (mg) | Decadron (mg) |
|---|---|---|---|---|---|
| 1 | 1000 | 133 | 200 | 5 | 3 |
| 2 | 1000 | 67 | 200 | 5 | 3 |
| 3 | 1000 | 67 | 150 | 5 | 2 |
| 4 | 750 | 50 | 100 | 5 | 2 |
| 5 | 750 | 50 | 50 | 5 | 1 |
| 6 | 500 | 33 | 0 | 5 | 0 |
| 7 | 500 | 25 | 0 | 5 | 0 |

In some embodiments, the single formulation comprises acetaminophen, ibuprofen, gabapentin, and famotidine according to the formulations of Table 3.

TABLE 3

| | Acetaminophen (mg) | Ibuprofen (mg) | Gabapentin (mg) | Famotidine (mg) |
|---|---|---|---|---|
| 1 | 1000 | 300 | 100 | 5 |
| 2 | 750 | 200 | 50 | 5 |
| 3 | 500 | 150 | 33 | 5 |
| 4 | 300 | 100 | 0 | 5 |

In some embodiments, the single formulation comprises acetaminophen and ibuprofen, according to the formulations of Table 4.

TABLE 4

| | Acetaminophen (mg) | Ibuprofen (mg) |
|---|---|---|
| 1 | 600 | 400 |
| 2 | 500 | 300 |
| 3 | 425 | 260 |

TABLE 4-continued

| | Acetaminophen (mg) | Ibuprofen (mg) |
|---|---|---|
| 4 | 320 | 200 |
| 5 | 240 | 150 |
| 6 | 200 | 130 |
| 7 | 175 | 100 |
| 8 | 160 | 100 |
| 9 | 160 | 85 |
| 10 | 120 | 75 |
| 11 | 100 | 70 |
| 12 | 80 | 50 |
| 13 | 50 | 40 |

In some embodiments, the single formulation comprises acetaminophen, meloxicam, gabapentin, famotidine, and decadron, according to the formulations of Table 5. In certain embodiments, the single formulations of Table 5 are used for patients who are sulfa allergic and unable to ingest traditional non-steroidal anti-inflammatory drugs.

TABLE 5

| | Acetaminophen (mg) | Meloxicam (mg) | Gabapentin (mg) | Famotidine (mg) | Decadron (mg) |
|---|---|---|---|---|---|
| 1 | 1000 | 5 | 200 | 5 | 3 |
| 2 | 1000 | 5 | 200 | 5 | 3 |
| 3 | 1000 | 4 | 150 | 5 | 2 |
| 4 | 750 | 3 | 100 | 5 | 2 |
| 5 | 750 | 2 | 50 | 5 | 1 |
| 6 | 500 | 2 | 0 | 5 | 0 |
| 7 | 500 | 2 | 0 | 5 | 0 |

In some embodiments, the single formulation comprises acetaminophen, meloxicam, gabapentin, and famotidine, according to the formulations of Table 6. In certain embodiments, the single formulations of Table 6 are used for patients who are sulfa allergic and unable to ingest traditional non-steroidal anti-inflammatory drugs.

TABLE 6

| | Acetaminophen (mg) | Meloxicam (mg) | Gabapentin (mg) | Famotidine (mg) |
|---|---|---|---|---|
| 1 | 1000 | 5 | 200 | 5 |
| 2 | 1000 | 5 | 200 | 5 |
| 3 | 1000 | 4 | 150 | 5 |
| 4 | 750 | 3 | 100 | 5 |
| 5 | 750 | 3 | 100 | 5 |
| 6 | 500 | 2 | 50 | 5 |
| 7 | 500 | 2 | 0 | 5 |
| 8 | 500 | 2 | 0 | 5 |

In some embodiments, the single formulation comprises acetaminophen, celebrex, and gabapentin, according to the formulations of Table 7. In some embodiments, the formulations of Table 7 are administered to a patient as part of post-operative treatment regime.

TABLE 7

| Dose # | Acetaminophen (mg) | Celebrex (mg) | Gabapentin (mg) |
|---|---|---|---|
| 1 | 1000 | 133 | 200 |
| 2 | 1000 | 133 | 200 |
| 3 | 1000 | 133 | 200 |
| 24 hour cumulative dose | 3000 | 399 | 600 |
| 4 | 1000 | 67 | 200 |
| 5 | 1000 | 67 | 200 |
| 6 | 1000 | 67 | 200 |

TABLE 7-continued

| Dose # | Acetaminophen (mg) | Celebrex (mg) | Gabapentin (mg) |
|---|---|---|---|
| 24 hour cumulative dose | 3000 | 201 | 600 |
| 7 | 1000 | 67 | 150 |
| 8 | 1000 | 67 | 150 |
| 9 | 1000 | 67 | 150 |
| 24 hour cumulative dose | 3000 | 201 | 450 |
| 10 | 750 | 50 | 100 |
| 11 | 750 | 50 | 100 |
| 12 | 750 | 50 | 100 |
| 24 hour cumulative dose | 2250 | 150 | 300 |
| 13 | 750 | 50 | 50 |
| 14 | 750 | 50 | 50 |
| 15 | 750 | 50 | 50 |
| 24 hour cumulative dose | 2250 | 150 | 150 |
| 16 | 500 | 33 | 0 |
| 17 | 500 | 33 | 0 |
| 18 | 500 | 33 | 0 |
| 24 hour cumulative dose | 1500 | 99 | 0 |
| 19 | 500 | 25 | 0 |
| 20 | 500 | 25 | 0 |
| 21 | 500 | 25 | 0 |
| 24 hour cumulative dose | 1500 | 75 | 0 |

In some embodiments, the single formulation comprises acetaminophen, celebrex, gabapentin, famotidine, and decadron according to the formulations of Table 8. In some embodiments, the formulations of Table 8. In certain embodiments, the formulations in Table 8 can be used to treat patients who suffer from back pain, ankle sprains, and other minor injuries that may or may not require surgical intervention.

TABLE 8

| Dose # | Acetaminophen (mg) | Celebrex (mg) | Gabapentin (mg) | Famotidine (mg) | Decadron (mg) |
|---|---|---|---|---|---|
| 1 | 1000 | 133 | 200 | 5 | 3 |
| 2 | 1000 | 133 | 200 | 5 | 3 |
| 3 | 1000 | 133 | 200 | 5 | 3 |
| 24 hour cumulative dose | 3000 | 399 | 600 | 15 | 9 |
| 4 | 1000 | 67 | 200 | 5 | 3 |
| 5 | 1000 | 67 | 200 | 5 | 3 |
| 6 | 1000 | 67 | 200 | 5 | 3 |
| 24 hour cumulative dose | 3000 | 201 | 600 | 15 | 9 |
| 7 | 1000 | 67 | 150 | 5 | 2 |
| 8 | 1000 | 67 | 150 | 5 | 2 |
| 9 | 1000 | 67 | 150 | 5 | 2 |
| 24 hour cumulative dose | 3000 | 201 | 450 | 15 | 6 |
| 10 | 750 | 50 | 100 | 5 | 2 |
| 11 | 750 | 50 | 100 | 5 | 2 |
| 12 | 750 | 50 | 100 | 5 | 2 |
| 24 hour cumulative dose | 2250 | 150 | 300 | 15 | 6 |
| 13 | 750 | 50 | 50 | 5 | 1 |
| 14 | 750 | 50 | 50 | 5 | 1 |
| 15 | 750 | 50 | 50 | 5 | 1 |
| 24 hour cumulative dose | 2250 | 150 | 150 | 15 | 3 |
| 16 | 500 | 33 | 0 | 5 | 0 |
| 17 | 500 | 33 | 0 | 5 | 0 |
| 18 | 500 | 33 | 0 | 5 | 0 |
| 24 hour cumulative dose | 1500 | 99 | 0 | 15 | 0 |
| 19 | 500 | 25 | 0 | 5 | 0 |
| 20 | 500 | 25 | 0 | 5 | 0 |
| 21 | 500 | 25 | 0 | 5 | 0 |
| 24 hour cumulative dose | 1500 | 75 | 0 | 15 | 0 |

In some embodiments, the single formulation comprises acetaminophen, celebrex, gabapentin, and famotidine according to the formulations of Table 9. In some embodiments, the formulations of Table 9 are administered to a patient as part of dental pain treatment regime.

TABLE 9

| Dose # | Acetaminophen (mg) | Celebrex (mg) | Gabapentin (mg) | Famotidine (mg) |
|---|---|---|---|---|
| 1 | 1000 | 133 | 200 | 5 |
| 2 | 1000 | 133 | 200 | 5 |
| 3 | 1000 | 133 | 200 | 5 |
| 24 hour cumulative dose | 3000 | 399 | 600 | 15 |
| 4 | 1000 | 67 | 150 | 5 |
| 5 | 1000 | 67 | 150 | 5 |
| 6 | 1000 | 67 | 150 | 5 |
| 24 hour cumulative dose | 3000 | 201 | 450 | 15 |
| 7 | 750 | 67 | 100 | 5 |
| 8 | 750 | 67 | 100 | 5 |
| 9 | 750 | 67 | 100 | 5 |
| 24 hour cumulative dose | 2250 | 201 | 300 | 15 |
| 10 | 500 | 50 | 50 | 5 |
| 11 | 500 | 50 | 50 | 5 |
| 12 | 500 | 50 | 50 | 5 |
| 24 hour cumulative dose | 1500 | 150 | 150 | 15 |
| 13 | 500 | 50 | 50 | 5 |
| 14 | 500 | 50 | 50 | 5 |
| 15 | 500 | 50 | 50 | 5 |
| 24 hour cumulative dose | 1500 | 150 | 150 | 15 |

In some embodiments, the single formulation comprises acetaminophen, celebrex, gabapentin, and famotidine according to the formulations of Table 10. In some embodiments, the formulations of Table 10 are administered to a patient after the birth of a child by either vaginal delivery or Caesarean section.

TABLE 10

| Dose # | Acetaminophen (mg) | Celebrex (mg) | Gabapentin (mg) | Famotidine (mg) |
|---|---|---|---|---|
| 1 | 1000 | 300 | 100 | 5 |
| 2 | 1000 | 300 | 100 | 5 |
| 3 | 1000 | 300 | 100 | 5 |
| 24 hour cumulative dose | 3000 | 900 | 300 | 15 |
| 4 | 1000 | 300 | 100 | 5 |
| 5 | 1000 | 300 | 100 | 5 |
| 6 | 1000 | 300 | 100 | 5 |
| 24 hour cumulative dose | 3000 | 900 | 300 | 15 |
| 7 | 750 | 200 | 50 | 5 |
| 8 | 750 | 200 | 50 | 5 |
| 9 | 750 | 200 | 50 | 5 |

TABLE 10-continued

| Dose # | Acetaminophen (mg) | Celebrex (mg) | Gabapentin (mg) | Famotidine (mg) |
|---|---|---|---|---|
| 24 hour cumulative dose | 2250 | 600 | 150 | 15 |
| 10 | 500 | 150 | 33 | 5 |
| 11 | 500 | 150 | 33 | 5 |
| 12 | 500 | 150 | 33 | 5 |
| 24 hour cumulative dose | 1500 | 450 | 99 | 15 |
| 13 | 300 | 100 | 0 | 5 |
| 14 | 300 | 100 | 0 | 5 |
| 15 | 300 | 100 | 0 | 5 |

In some embodiments, the single formulation comprises acetaminophen and ibuprofen according to the formulations of Table 11. In some embodiments, the formulations of Table 11 are given to a patient as part of pain treatment regime given to children. In some embodiments, the formulations are administered to children who weigh between 24 to 35 pounds.

TABLE 11

| Dose # | Acetaminophen (mg) | Ibuprofen (mg) |
|---|---|---|
| 1 | 200 | 130 |
| 2 | 200 | 130 |
| 3 | 200 | 130 |
| 24 hour cumulative dose | 600 | 390 |
| 4 | 175 | 100 |
| 5 | 175 | 100 |
| 6 | 175 | 100 |
| 24 hour cumulative dose | 525 | 300 |
| 7 | 160 | 85 |
| 8 | 160 | 85 |
| 9 | 160 | 85 |
| 24 hour cumulative dose | 480 | 255 |
| 10 | 100 | 70 |
| 11 | 100 | 70 |
| 12 | 100 | 70 |
| 24 hour cumulative dose | 300 | 210 |
| 13 | 50 | 40 |
| 14 | 50 | 40 |
| 15 | 50 | 40 |
| 24 hour cumulative dose | 150 | 120 |

In some embodiments, the single formulation comprises acetaminophen and ibuprofen according to the formulations of Table 12. In some embodiments, the formulations of Table 12 are given to a patient as part of pain treatment regime given to children. In some embodiments, the formulations are administered to children who weigh between 36 to 47 pounds.

TABLE 12

| Dose # | Acetaminophen (mg) | Ibuprofen (mg) |
|---|---|---|
| 1 | 320 | 200 |
| 2 | 320 | 200 |
| 3 | 320 | 200 |
| 24 hour cumulative dose | 960 | 600 |
| 4 | 240 | 150 |
| 5 | 240 | 150 |
| 6 | 240 | 150 |
| 24 hour cumulative dose | 720 | 450 |
| 7 | 160 | 100 |
| 8 | 160 | 100 |
| 9 | 160 | 100 |
| 24 hour cumulative dose | 480 | 300 |
| 10 | 120 | 75 |
| 11 | 120 | 75 |
| 12 | 120 | 75 |

TABLE 12-continued

| Dose # | Acetaminophen (mg) | Ibuprofen (mg) |
|---|---|---|
| 24 hour cumulative dose | 360 | 225 |
| 13 | 80 | 50 |
| 14 | 80 | 50 |
| 15 | 80 | 50 |
| 24 hour cumulative dose | 240 | 150 |

In some embodiments, the single formulation comprises acetaminophen and ibuprofen according to the formulations of Table 13. In some embodiments, the formulations of Table 13 are given to a patient as part of pain treatment regime given to children. In some embodiments, the formulations are administered to children who weigh between 48 to 59 pounds.

TABLE 13

| Dose # | Acetaminophen (mg) | Ibuprofen (mg) |
|---|---|---|
| 1 | 425 | 260 |
| 2 | 425 | 260 |
| 3 | 425 | 260 |
| 24 hour cumulative dose | 1275 | 780 |
| 4 | 320 | 200 |
| 5 | 320 | 200 |
| 6 | 320 | 200 |
| 24 hour cumulative dose | 960 | 600 |
| 7 | 240 | 150 |
| 8 | 240 | 150 |
| 9 | 240 | 150 |
| 24 hour cumulative dose | 720 | 450 |
| 10 | 160 | 100 |
| 11 | 160 | 100 |
| 12 | 160 | 100 |
| 24 hour cumulative dose | 480 | 300 |
| 13 | 120 | 75 |
| 14 | 120 | 75 |
| 15 | 120 | 75 |
| 24 hour cumulative dose | 360 | 225 |

In some embodiments, the single formulation comprises acetaminophen and ibuprofen according to the formulations of Table 14. In some embodiments, the formulations of Table 14 are given to a patient as part of pain treatment regime given to children. In some embodiments, the formulations are administered to children who weigh between 60 to 71 pounds.

TABLE 14

| Dose # | Acetaminophen (mg) | Ibuprofen (mg) |
|---|---|---|
| 1 | 500 | 300 |
| 2 | 500 | 300 |
| 3 | 500 | 300 |
| 24 hour cumulative dose | 1500 | 900 |
| 4 | 425 | 260 |
| 5 | 425 | 260 |
| 6 | 425 | 260 |
| 24 hour cumulative dose | 1275 | 780 |
| 7 | 320 | 200 |
| 8 | 320 | 200 |
| 9 | 320 | 200 |
| 24 hour cumulative dose | 960 | 600 |
| 10 | 240 | 150 |
| 11 | 240 | 150 |
| 12 | 240 | 150 |
| 24 hour cumulative dose | 720 | 450 |
| 13 | 160 | 100 |
| 14 | 160 | 100 |
| 15 | 160 | 100 |
| 24 hour cumulative dose | 480 | 300 |

In some embodiments, the single formulation comprises acetaminophen and ibuprofen according to the formulations of Table 15. In some embodiments, the formulations of Table 15 are given to a patient as part of pain treatment regime given to children. In some embodiments, the formulations are administered to children who weigh between 72 to 95 pounds.

TABLE 15

| Dose # | Acetaminophen (mg) | Ibuprofen (mg) |
|---|---|---|
| 1 | 600 | 400 |
| 2 | 600 | 400 |
| 3 | 600 | 400 |
| 24 hour cumulative dose | 1800 | 1200 |
| 4 | 500 | 300 |
| 5 | 500 | 300 |
| 6 | 500 | 300 |
| 24 hour cumulative dose | 1500 | 900 |
| 7 | 425 | 260 |
| 8 | 425 | 260 |
| 9 | 425 | 260 |
| 24 hour cumulative dose | 1275 | 780 |
| 10 | 320 | 200 |
| 11 | 320 | 200 |
| 12 | 320 | 200 |
| 24 hour cumulative dose | 960 | 600 |
| 13 | 240 | 150 |
| 14 | 240 | 150 |
| 15 | 240 | 150 |
| 24 hour cumulative dose | 720 | 450 |

In some embodiments, the single formulation of any of the previous embodiments is allocated to a patient throughout the day based on the number of hours in a day divided by the number of sides of the n-polygon or one or more m-polygons.

In some embodiments, the single formulation of any of the previous embodiments is allocated to a patient throughout the day based on the number of medicament chambers within a section of package.

In some embodiments, the single formulation of any of the previous embodiments is given to a patient on the first day every four hours. In some embodiments, the single formulation of any of the previous embodiments is given to a patient on the second day every six hours. In some embodiments, the single formulation of any of the previous embodiments is given to a patient on the third day every eight hours. In some embodiments, the single formulation of any of the previous embodiments is given to a patient on the fourth day every twelve hours. In some embodiments, the single formulation of any of the previous embodiments is given to a patient on the fifth day in a single dose.

In some embodiments, any of the previous formulations disclosed herein can be provided in the appropriate pharmaceutical composition and be administered by a suitable route of administration.

In some embodiments, any of the previous formulations can be used to treat a patient to manage pain associated with a COVID-19 infection.

In some embodiments, any of the previous formulations can be used to treat a patient to manage pain, wherein the patient is also infected with COVID-19.

In some embodiments, the single formulations provided herein may be administered by any conventional route, in particular orally, parenterally, rectally or by inhalation (e.g. in the form of aerosols). In certain embodiments, the single formulations provided herein is administered orally.

In some embodiments, the single formulations may be used as solid compositions for oral administration, of tablets, pills, hard gelatin capsules, powders or granules of the single formulations. In certain embodiments, the single formulations are mixed with one or more inert diluents or adjuvants, such as sucrose, lactose or starch.

In some embodiments, the single formulations comprise substances other than diluents, for example a lubricant, such as magnesium stearate, or a coating intended for controlled release.

In some embodiments, the single formulations are used as liquid formulations for oral administration, of solutions which are pharmaceutically acceptable, suspensions, emulsions, syrups and elixirs containing inert diluents, such as water or liquid paraffin. These formulations can also comprise substances other than diluents, for example wetting, sweetening or flavoring products.

In some embodiments, the single formulations comprise adjuvants, in particular wetting, isotonizing, emulsifying, dispersing and stabilizing agents. In certain embodiments, the single formulations are sterilized. Sterilization can be carried out in several ways, for example using a bacteriological filter, by radiation or by heating. They can also be prepared in the form of sterile solid compositions which can be dissolved at the time of use in sterile water or any other injectable sterile medium.

In some embodiments, the single formulations can also be aerosols. For use in the form of liquid aerosols, the compositions can be stable sterile solutions or solid compositions dissolved at the time of use in apyrogenic sterile water, in saline or any other pharmaceutically acceptable vehicle.

In certain embodiments, a single formulation provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

In some embodiments, the single formulations comprise anhydrous single formulations and dosage forms wherein anhydrous or low moisture containing ingredients and low moisture or low humidity conditions are used. Pharmaceutical compositions and dosage forms that comprise lactose and at least one active ingredient that comprises a primary or secondary amine can be anhydrous if substantial contact with moisture and/or humidity during manufacturing, packaging, and/or storage is expected. An anhydrous single formulation should be prepared and stored such that its anhydrous nature is maintained. Accordingly, anhydrous compositions can be packaged using materials known to prevent exposure to water such that they can be included in suitable formulary kits.

In some embodiments, the single formulations comprise one or more compounds that reduce the rate by which an active ingredient will decompose. Such compounds, which are referred to herein as "stabilizers," include, but not limited to, antioxidants such as ascorbic acid, pH buffers, or salt buffers.

In some embodiments, the single formulations can take the form comprising solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, for example, an animal subject, such as a mammalian subject, for example, a human subject.

In some embodiments, the single formulations are formulated to be compatible with its intended route of administration. Examples of routes of administration include, but not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

Examples of dosage forms include, but not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington's Pharmaceutical Sciences, 20th ed., Mack Publishing, Easton Pa. (2000).

Generally, the ingredients of the single formulations are supplied either separately or mixed together in unit dosage form, for example, as a dry lyophilized powder or water free concentrate in a hermetically sealed container such as an ampoule or sachette indicating the quantity of active agent. Where the single formulations are to be administered by infusion, it can be dispensed with an infusion bottle containing sterile pharmaceutical grade water or saline. Where the single formulations are administered by injection, an ampoule of sterile water for injection or saline can be provided so that the ingredients may be mixed prior to administration.

Oral Dosage Forms

In some embodiments, the single formulations comprise compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000).

In certain embodiments, the single formulations comprise oral dosage forms are solid and prepared under anhydrous conditions with anhydrous ingredients, as described in detail in the sections above. However, the scope of the compositions provided herein extends beyond anhydrous, solid oral dosage forms. As such, further forms are described herein.

In certain embodiments, the single formulations comprise oral dosage forms that are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

In some embodiments, the single formulations comprise fillers. Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

Delayed Release Dosage Forms

In some embodiments, the single formulations can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gelcaps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using a transdermal patch, liposomes, or other modes of administration. In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (Science 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, $16^{th}$, 18th and $20^{th}$ eds., Mack Publishing, Easton Pa. (1980, 1990 & 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Physician's Desk Reference (PDR) $57^{th}$ Ed., 2003, Medical Economics Co., Inc., Montvale, N.J., which are incorporated herein by reference in its entirety.

Prophetic Clinical Example 1

Consent will be obtained from patients to participate in clinical trials or their parents if minors. Approximately 100 adults (18 years and older) and 100 children (between the ages of 6-17) who are post-surgical or emergency room patients will be selected. These patients will have minor reversible injuries, causing pain that require pain management. The patients will be randomly assigned to one of two conditions.

The first condition will consist of patients that receive traditional opioid pain medications. The second condition will provide a non-opioid pain management regime as described in the following paragraphs. The aforementioned conditions will be statistically compared to determine if there are significant differences. In general, surgeries and injuries include but are not limited to: (a) dental, (b) orthopedic, (c) cesarean sections, (d) general surgery, (e) vaginal deliveries, (f) back injuries, (g) shoulder injuries, (h) knee injuries, (i) and various types of physical trauma to the body. Due to the nature of the study, there will be no control group because it is medically inappropriate to withhold pain medication after surgery or injury.

Participant exclusion criteria include but are not limited to: (a) chronic opioid usage, (b) opioid addiction, (c) history of chronic pain, and (d) medical contraindications (e.g. kidney issues, limited liver or kidney function, and allergies to medications contained within Algia).

Individual doses of opioid medications (condition 1) will be administered in accordance to hospital policy. Individual doses of the appropriate pharmaceutical formulations will be determined by weight and safety of administration with respect to other medical conditions and self-reported pain levels indicated by the Numeric Rating Scale (NRS-11). For adult participants, doses will range from Acetaminophen at 325 mg-1000 mg for medication 1, Celecoxib at 50 mg-200 mg for medication 2 (or alternatively Ibuprofen at 100 mg-300 mg for medication 2), Gabapentin at 50 mg-200 mg for medication 3, Famotidine at 5-15 mg for medication 4 and Dexamethasone at 4-8 mg for medication 5.

For children, doses will range from Acetaminophen at 50 mg-600 mg for medication 1 and Ibuprofen at 40 mg-400 mg for medication 2.

Dosing intervals for opioid medications will be consistent with hospital guidelines. (See Effective Management of Acute Pain Recommendations from the Ad Hoc Committee on Pain Management and Prescription Drug Abuse; Pino, C. A. et al.)

The single formulation comprising acetaminophen, celecoxib, gabapentin, famotidine, and dexamethasone according to the formulations of Table 16 will be given to adults post-injury.

TABLE 16

| Dose | Day | Time Point (Hours) | Drug Administration |
|---|---|---|---|
| 1 | 1 | 0 | Acetaminophen 1000 mg<br>Celecoxib 133 mg<br>Gabapentin 200 mg<br>Famotidine 5 mg<br>Dexamethasone 3 mg |
| 2 | 1 | 8 | Acetaminophen 1000 mg<br>Celecoxib 133 mg<br>Gabapentin 200 mg<br>Famotidine 5 mg<br>Dexamethasone 3 mg |
| 3 | 1 | 16 | Acetaminophen 1000 mg<br>Celecoxib 133 mg<br>Gabapentin 200 mg<br>Famotidine 5 mg<br>Dexamethasone 3 mg |
| 4 | 2 | 24 | Acetaminophen 1000 mg<br>Celecoxib 67 mg<br>Gabapentin 200 mg<br>Famotidine 5 mg<br>Dexamethasone 3 mg |
| 5 | 2 | 32 | Acetaminophen 1000 mg<br>Celecoxib 67 mg<br>Gabapentin 200 mg<br>Famotidine 5 mg<br>Dexamethasone 3 mg |
| 6 | 2 | 40 | Acetaminophen 1000 mg<br>Celecoxib 67 mg<br>Gabapentin 200 mg<br>Famotidine 5 mg<br>Dexamethasone 3 mg |
| 7 | 3 | 48 | Acetaminophen 1000 mg<br>Celecoxib 67 mg<br>Gabapentin 150 mg<br>Famotidine 5 mg<br>Dexamethasone 2 mg |
| 8 | 3 | 56 | Acetaminophen 1000 mg<br>Celecoxib 67 mg<br>Gabapentin 150 mg<br>Famotidine 5 mg<br>Dexamethasone 2 mg |
| 9 | 3 | 64 | Acetaminophen 1000 mg<br>Celecoxib 67 mg<br>Gabapentin 150 mg<br>Famotidine 5 mg<br>Dexamethasone 2 mg |
| 10 | 4 | 72 | Acetaminophen 750 mg<br>Celecoxib 50 mg<br>Gabapentin 100 mg<br>Famotidine 5 mg<br>Dexamethasone 2 mg |
| 11 | 4 | 80 | Acetaminophen 750 mg<br>Celecoxib 50 mg<br>Gabapentin 100 mg<br>Famotidine 5 mg<br>Dexamethasone 2 mg |
| 12 | 4 | 88 | Acetaminophen 750 mg<br>Celecoxib 50 mg<br>Gabapentin 100 mg<br>Famotidine 5 mg<br>Dexamethasone 2 mg |
| 13 | 5 | 96 | Acetaminophen 750 mg<br>Celecoxib 50 mg<br>Gabapentin 50 mg<br>Famotidine 5 mg<br>Dexamethasone 1 mg |
| 14 | 5 | 104 | Acetaminophen 750 mg<br>Celecoxib 50 mg<br>Gabapentin 50 mg<br>Famotidine 5 mg<br>Dexamethasone 1 mg |
| 15 | 5 | 112 | Acetaminophen 750 mg<br>Celecoxib 50 mg<br>Gabapentin 50 mg<br>Famotidine 5 mg<br>Dexamethasone 1 mg |
| 16 | 6 | 120 | Acetaminophen 500 mg<br>Celecoxib 33 mg<br>Famotidine 5 mg |
| 17 | 6 | 128 | Acetaminophen 500 mg<br>Celecoxib 33 mg<br>Famotidine 5 mg |
| 18 | 6 | 136 | Acetaminophen 500 mg<br>Celecoxib 33 mg<br>Famotidine 5 mg |
| 19 | 7 | 144 | Acetaminophen 500 mg<br>Celecoxib 25 mg<br>Famotidine 5 mg |
| 20 | 7 | 152 | Acetaminophen 500 mg<br>Celecoxib 25 mg<br>Famotidine 5 mg |

TABLE 16-continued

| Dose | Day | Time Point (Hours) | Drug Administration |
|---|---|---|---|
| 21 | 7 | 160 | Acetaminophen 500 mg<br>Celecoxib 25 mg<br>Famotidine 5 mg |

The single formulation comprising acetaminophen, celecoxib, gabapentin, and famotidine according to the formulations of Table 17 will be given to adults post-injury.

TABLE 17

| Dose | Day | Time (Hours) | Drug Administration |
|---|---|---|---|
| 1 | 1 | 0 | Acetaminophen 1000 mg<br>Celecoxib 133 mg<br>Gabapentin 200 mg<br>Famotidine 5 mg |
| 2 | 1 | 8 | Acetaminophen 1000 mg<br>Celecoxib 133 mg<br>Gabapentin 200 mg<br>Famotidine 5 mg |
| 3 | 1 | 16 | Acetaminophen 1000 mg<br>Celecoxib 133 mg<br>Gabapentin 200 mg<br>Famotidine 5 mg |
| 4 | 2 | 24 | Acetaminophen 1000 mg<br>Celecoxib 67 mg<br>Gabapentin 200 mg<br>Famotidine 5 mg |
| 5 | 2 | 32 | Acetaminophen 1000 mg<br>Celecoxib 67 mg<br>Gabapentin 200 mg<br>Famotidine 5 mg |
| 6 | 2 | 40 | Acetaminophen 1000 mg<br>Celecoxib 67 mg<br>Gabapentin 200 mg<br>Famotidine 5 mg |
| 7 | 3 | 48 | Acetaminophen 1000 mg<br>Celecoxib 67 mg<br>Gabapentin 150 mg<br>Famotidine 5 mg |
| 8 | 3 | 56 | Acetaminophen 1000 mg<br>Celecoxib 67 mg<br>Gabapentin 150 mg<br>Famotidine 5 mg |
| 9 | 3 | 64 | Acetaminophen 1000 mg<br>Celecoxib 67 mg<br>Gabapentin 150 mg<br>Famotidine 5 mg |
| 10 | 4 | 72 | Acetaminophen 750 mg<br>Celecoxib 50 mg<br>Gabapentin 100 mg<br>Famotidine 5 mg |
| 11 | 4 | 80 | Acetaminophen 750 mg<br>Celecoxib 50 mg<br>Gabapentin 100 mg<br>Famotidine 5 mg |
| 12 | 4 | 88 | Acetaminophen 750 mg<br>Celecoxib 50 mg<br>Gabapentin 100 mg<br>Famotidine 5 mg |
| 13 | 5 | 96 | Acetaminophen 750 mg<br>Celecoxib 50 mg<br>Gabapentin 50 mg<br>Famotidine 5 mg |
| 14 | 5 | 104 | Acetaminophen 750 mg<br>Celecoxib 50 mg<br>Gabapentin 50 mg<br>Famotidine 5 mg |
| 15 | 5 | 112 | Acetaminophen 750 mg<br>Celecoxib 50 mg<br>Gabapentin 50 mg<br>Famotidine 5 mg |
| 16 | 6 | 120 | Acetaminophen 500 mg<br>Celecoxib 33 mg<br>Famotidine 5 mg |
| 17 | 6 | 128 | Acetaminophen 500 mg<br>Celecoxib 33 mg<br>Famotidine 5 mg |
| 18 | 6 | 136 | Acetaminophen 500 mg<br>Celecoxib 33 mg<br>Famotidine 5 mg |
| 19 | 7 | 144 | Acetaminophen 500 mg<br>Celecoxib 25 mg<br>Famotidine 5 mg |
| 20 | 7 | 152 | Acetaminophen 500 mg<br>Celecoxib 25 mg<br>Famotidine 5 mg |
| 21 | 7 | 162 | Acetaminophen 500 mg<br>Celecoxib 25 mg<br>Famotidine 5 mg |

The single formulation comprising acetaminophen, celecoxib, gabapentin, and famotidine according to the formulations of Table 18 will be given to adults post-dental procedure/injury.

TABLE 18

| Dose | Day | Time (Hours) | Drug Administration |
|---|---|---|---|
| 1 | 1 | 0 | Acetaminophen 1000 mg<br>Celecoxib 133 mg<br>Gabapentin 200 mg<br>Famotidine 5 mg |
| 2 | 1 | 8 | Acetaminophen 1000 mg<br>Celecoxib 133 mg<br>Gabapentin 200 mg<br>Famotidine 5 mg |
| 3 | 1 | 16 | Acetaminophen 1000 mg<br>Celecoxib 133 mg<br>Gabapentin 200 mg<br>Famotidine 5 mg |
| 4 | 2 | 24 | Acetaminophen 1000 mg<br>Celecoxib 67 mg<br>Gabapentin 150 mg<br>Famotidine 5 mg |
| 5 | 2 | 32 | Acetaminophen 1000 mg<br>Celecoxib 67 mg<br>Gabapentin 150 mg<br>Famotidine 5mg |
| 6 | 2 | 40 | Acetaminophen 1000 mg<br>Celecoxib 67 mg<br>Gabapentin 150 mg<br>Famotidine 5 mg |

TABLE 18-continued

| Dose | Day | Time (Hours) | Drug Administration |
|---|---|---|---|
| 7 | 3 | 48 | Acetaminophen 750 mg<br>Celecoxib 67 mg<br>Gabapentin 100 mg<br>Famotidine 5 mg |
| 8 | 3 | 56 | Acetaminophen 750 mg<br>Celecoxib 67 mg<br>Gabapentin 100 mg<br>Famotidine 5 mg |
| 9 | 3 | 64 | Acetaminophen 750 mg<br>Celecoxib 67 mg<br>Gabapentin 100 mg<br>Famotidine 5 mg |
| 10 | 4 | 72 | Acetaminophen 750 mg<br>Celecoxib 50 mg<br>Gabapentin 50 mg<br>Famotidine 5 mg |
| 11 | 4 | 80 | Acetaminophen 500 mg<br>Celecoxib 50 mg<br>Gabapentin 50 mg<br>Famotidine 5 mg |
| 12 | 4 | 88 | Acetaminophen 500 mg<br>Celecoxib 50 mg<br>Gabapentin 50 mg<br>Famotidine 5mg |
| 13 | 5 | 96 | Acetaminophen 500 mg<br>Celecoxib 50 mg<br>Gabapentin 50 mg<br>Famotidine 5 mg |
| 14 | 5 | 104 | Acetaminophen 500 mg<br>Celecoxib 50 mg<br>Gabapentin 50 mg<br>Famotidine 5 mg |
| 15 | 5 | 112 | Acetaminophen 500 mg<br>Celecoxib 50 mg<br>Gabapentin 50 mg<br>Famotidine 5 mg |

The single formulation comprising acetaminophen, celecoxib, gabapentin, and famotidine according to the formulations of Table 19 will be given to adults post-OB procedure or vaginal birth.

TABLE 19

| Dose | Day | Time (Hours) | Drug Administration |
|---|---|---|---|
| 1 | 1 | 0 | Acetaminophen 1000 mg<br>Ibuprofen 300 mg<br>Gabapentin 100 mg<br>Famotidine 5 mg |
| 2 | 1 | 8 | Acetaminophen 1000 mg<br>Ibuprofen 300 mg<br>Gabapentin 100 mg<br>Famotidine 5 mg |
| 3 | 1 | 16 | Acetaminophen 1000 mg<br>Ibuprofen 300 mg<br>Gabapentin 100 mg<br>Famotidine 5 mg |
| 4 | 2 | 24 | Acetaminophen 1000 mg<br>Ibuprofen 300 mg<br>Gabapentin 100 mg<br>Famotidine 5 mg |
| 5 | 2 | 32 | Acetaminophen 1000 mg<br>Ibuprofen 300 mg<br>Gabapentin 100 mg<br>Famotidine 5 mg |
| 6 | 2 | 40 | Acetaminophen 1000 mg<br>Ibuprofen 300 mg<br>Gabapentin 100 mg<br>Famotidine 5 mg |
| 7 | 3 | 48 | Acetaminophen 750 mg<br>Ibuprofen 200 mg<br>Gabapentin 50 mg<br>Famotidine 5 mg |
| 8 | 3 | 56 | Acetaminophen 750 mg<br>Ibuprofen 200 mg<br>Gabapentin 50 mg<br>Famotidine 5 mg |
| 9 | 3 | 64 | Acetaminophen 750 mg<br>Ibuprofen 200 mg<br>Gabapentin 50 mg<br>Famotidine 5 mg |
| 10 | 4 | 72 | Acetaminophen 500 mg<br>Ibuprofen 150 mg<br>Gabapentin 33 mg<br>Famotidine 5 mg |
| 11 | 4 | 80 | Acetaminophen 500 mg<br>Ibuprofen 150 mg<br>Gabapentin 33 mg<br>Famotidine 5 mg |
| 12 | 4 | 88 | Acetaminophen 500 mg<br>Ibuprofen 150 mg<br>Gabapentin 33 mg<br>Famotidine 5 mg |
| 13 | 5 | 96 | Acetaminophen 300 mg<br>Ibuprofen 100 mg<br>Famotidine 5 mg |
| 14 | 5 | 104 | Acetaminophen 300 mg<br>Ibuprofen 100 mg<br>Famotidine 5 mg |
| 15 | 5 | 112 | Acetaminophen 300 mg<br>Ibuprofen 100 mg<br>Famotidine 5 mg |

Condition 2 is ideal for dosing children as follows. In some embodiments, the single formulation comprising acetaminophen and ibuprofen according to the formulations of Table 20 will be given to children. Weight based dosing for pediatric patients is essential in order to optimize safety profile and dose medications well under maximum dose allowable while maintaining efficacy. This table demonstrates dosing in a child that is approximately 60-71 pounds in weight.

TABLE 20

| DOSE | DAY | TIME (HOURS) | DRUG ADMINISTRATIONS |
|---|---|---|---|
| 1 | 1 | 0 | Acetaminophen 500 mg<br>Celecoxib 67 mg<br>Omeprazole 20 mg |
| 2 | 1 | 8 | Acetaminophen 500 mg<br>Celecoxib 67 mg<br>Omeprazole 20 mg |

TABLE 20-continued

| DOSE | DAY | TIME (HOURS) | DRUG ADMINISTRATIONS |
|---|---|---|---|
| 3 | 1 | 16 | Acetaminophen 500 mg<br>Celecoxib 67 mg<br>Omeprazole 20 mg |
| 4 | 2 | 24 | Acetaminophen 425 mg<br>Celecoxib 50 mg<br>Omeprazole 20 mg |
| 5 | 2 | 32 | Acetaminophen 425 mg<br>Celecoxib 50 mg<br>Omeprazole 20 mg |
| 6 | 2 | 40 | Acetaminophen 425 mg<br>Celecoxib 50 mg<br>Omeprazole 20 mg |
| 7 | 3 | 48 | Acetaminophen 320 mg<br>Celecoxib 40 mg<br>Omeprazole 20 mg |
| 8 | 3 | 56 | Acetaminophen 320 mg<br>Celecoxib 40 mg<br>Omeprazole 20 mg |
| 9 | 3 | 64 | Acetaminophen 320 mg<br>Celecoxib 40 mg<br>Omeprazole 20 mg |
| 10 | 4 | 72 | Acetaminophen 240 mg<br>Celecoxib 25 mg<br>Omeprazole 20 mg |
| 11 | 4 | 80 | Acetaminophen 240 mg<br>Celecoxib 25 mg<br>Omeprazole 20 mg |
| 12 | 4 | 88 | Acetaminophen 240 mg<br>Celecoxib 25 mg<br>Omeprazole 20 mg |
| 13 | 5 | 96 | Acetaminophen 160 mg<br>Celecoxib 10 mg<br>Omeprazole 20 mg |
| 14 | 5 | 104 | Acetaminophen 160 mg<br>Celecoxib 10 mg<br>Omeprazole 20 mg |
| 15 | 5 | 112 | Acetaminophen 160 mg<br>Celecoxib 10 mg<br>Omeprazole 20 mg |

Pain Assessment Protocol: In all administrations of the single formulation, patients being administered the compositions of any of the previous embodiments, will self-report their pain levels using the Numeric Rating Scale (NRS-11). The NRS-11 is an 11-point scale for self-reporting levels of pain indicated by the level of interference with the ability to perform daily activities (ADLs). The NRS-11 is currently used for adults and children 10 years and older. Table 21 classifies the numerical rating for pain.

TABLE 21

| Rating | Pain Level |
|---|---|
| 0 | No Pain |
| 1-3 | Mild Pain (Little interference with ADLs) |
| 4-6 | Moderate pain (Significant interference with ADLs) |
| 7-10 | Severe pain (Unable to perform ADLs, disabling) |

In certain cases, intervention adherence will be assessed by explicitly asking the participant if they were adhering to the prescribed medication regimen as an additional self-report question following the self-report section of the NRS-11.

In certain cases, patients will self-report pain levels before leaving hospital. After discharge from the hospital, patients will continue to self-report pain levels using the NRS-11 one hour after each dosage of medication by answering the NRS-11 by phone.

This protocol provides clinicians a reasonable alternative to opioid therapy. This reasonable alternative provides a more comprehensive medication amalgam that will increase pain management effectiveness without the use of opioids and the various issues that accompany opioid therapy (e.g. addiction, suppressed breathing, opioid-induced hyperalgesia, psychological dependence, and increased tolerance to opioids).

Capsule Compounding Example

In order to account for processing error considerations during preparation, an additional 5% of the required quantities of ingredients were measured. All calculations and preparations techniques were verified before each step.

The following compounds were used to make one capsule: Acetaminophen, USP (APAP; Paracetamol; N-(4-Hydroxyphenyl)acetamide), Ibuprofen, USP (IBU;2-(4-Isobutylphenyl)propionic acid), Gabapentin USP (1-(Aminomethyl)cyclohexaneacectic Acid, and Famotidine USP (3-[[[2-[(Aminoiminomethyl)amino]-4-thiazolyl]methyl]thio]-N-(aminosulfonyl)propanimidamid), and CapsuBlend™. Each of these compounds was purchased commercially from either Medisca or Letco.

Empty gelatin capsules were stored at room temperature at constant humidity. Filled, hard gelatin capsules were stored away from excessive heat.

Each compound powder was prepared using a mortar and pestle. The ingredients were weighed out using Ohaus Scout Portable Balance to about the desired amount of powder. Each ingredient was placed in the Wedgwood mortar, and tritrated by means of pestle to very fine powder. The fineness of the powder, as reflected in the particle size, was assessed by passing the fine powder through a 40 or 50 fine mesh strainer. By reducing the particle size, the surface area and specific surface were increased.

After each compound powder was prepared according to the process above, a uniform mixture of Acetaminophen, Ibuprofen, Gabapentin, Famotidine was used to make 10 capsules.

10 empty capsules (size #00) were placed on the balance and the average weight of an empty (blank) capsule was determined. Each of the following ingredients was placed on a scale according to Table 22 in the amounts listed.

TABLE 22

| Ingredient | Amount measured (mg) | Amount per each of the 10 individual capsule (mg) | W/W % |
|---|---|---|---|
| Acetaminophen | 5000 | 5 | 68 |
| Ibuprofen | 1500 | 150 | 20.4 |
| Gabapentin | 330 | 33 | 4.5 |
| Famotidine | 50 | 5 | 0.7 |
| CapsuBlendTM | 470 | 47 | 6.4 |

All the ingredients were measured together and the method of geometric dilution was used to mix acetaminophen, ibuprofen, gabapentin, famotidine in a glass mortar and pestle. By this method, the ingredients were combined and tritrated together to form a homogeneous powder blend. For two minutes, the ingredients were mixed by hand and the uniform mixture was transferred to a pill tile. Ten capsules were prepared using the mixture and 'punch method' to ensure that only 10 capsules slots have capsules while the remaining are plugged to ensure that no powder was inadvertently not captured. The powder mixture was placed on a pill tile and compressed by a spatula into a pile of powder with a uniform depth of about one-half the length of a capsule's body (the longer portion).

The mixture was placed into the capsule as follows. A Profiller® 1100 Filler and Orienter were used to make the 5 capsules. The Profiller® 1100 has the capacity to make 100 capsules at a time. To ensure only ten capsules were filled, 80 slots were covered and sealed. We first put the body sheet set provided by the manufacturer on the filler base. Next, we placed 10 capsules into the Orienter Tray. The Orienter Tray orients the capsules, so the base of the capsule is down, and the cap is facing up. The Orienter was placed on top of the capsule filling device and locked into place. The lever on the base is pulled and the capsules are dropped into place in the orienter. After the capsules are placed in the orienter base, we checked to ensure all the capsules were properly aligned and secured. Next, we separated the caps from the base using the locking plate. The lever was pulled on the base, which applied pressure on the bottom of the capsule allowing the removal of the caps. The lever was released allowing the capsule base to return to original position. Next, the powder tray was placed securely over the capsules. The powder tray is used to ensure the medication is contained over the capsule tray. The combined powdered medication was then placed on the tray. Using a spreader, the powder was spread evenly over the capsules. A weighted tampering device was used to lightly press over the capsules to ensure they are filled uniformly. Once filled, the tray was removed. The top of the capsules was reset over the bottoms and ensured it fit correctly. The machine aligned. Once aligned, pressure was applied on the top and bottom of the filler with both hands on either side and pressed together. This combined the caps and the capsule together. The top was removed, which took with it all the capsules from the base and flipped over and set on the table. The capsules faced up. Using a weighted Capsule Locker, the capsules were gently pressed to ensure they are all uniformly closed. The base was flipped over, and the top was removed by slightly rotating it, this will release the capsules. Finally, the capsules were dumped into a secure basket for dispensing.

The cap was placed on the capsule and the weight of each capsule was weighted to ensure that each capsule was approximately equal to the weight of the powder mixture plus weight of the empty capsule.

Caution was used to prevent finger marks from moisture given that the gelatin capsules are sensitive to the moisture and finger marks. Hands and fingers were kept dry and clean, prior to touching any capsules for the filling operation.

The capsules had a beyond use date of 25% of the time remaining on the product's expiration or 6 months (whichever was earlier).

The capsules were stored at a controlled room temperature and away from light and heat.

Quality Control was maintained by weighing the finished powder and capsules and ensuring that it closely matched the theoretical weight. Quality control was considered satisfied if the weight between the finished powder and capsules and the theoretical weight were within 5%.

All publications and patent applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter limited solely by the scope of the following claims, including equivalents thereof.

REFERENCES

Code of Federal Regulations, Title 21, Chapter 2, part 1300. Available at: https://deadiversion.usdoj.gov/21cfr/cfr/2100cfrt.htm FDA Innovation Challenge: Devices to Prevent and Treat Opioid Use Disorder, Jul. 9, 2019. Available at: https://fda.gov/about-fda/cdrh-innovation/fda-innovation-challenge-devices-prevent-and-treat-opioid-use-disorder Korff M, Jensen M P, Karoly P. Assessing global pain severity by self-report in clinical and health services research. Spine. 2000; 25:3140-3151. doi: 10.1097/00007632-200012150-00009

Krebs, E. E., Gravely, A., Nugent, S., Jensen, A. C., DeRonne, B., Goldsmith, E. S, Noorbaloochi, S. (2018). Effect of opioid vs non opioid medications on pain-related function in patients with chronic back pain or hip or knee osteoarthritis pain: The SPACE randomized clinical trial. *JAMA: Journal of the American Medical Association,* 319(9), 872-882. doi:http://dx.doi.org.ezproxylocal.library.nova.edu/10.1001/jama.2018.0899

Shanthanna, H., N. H. Strand, D. A. Provenzano, C. A. Lobo, S. Eldabe, A. Bhatia, J. Wegener, K. Curtis, S. P. Cohen, and S. Narouze. "Caring for patients with pain during the COVID-19 pandemic: consensus recommendations from an international expert panel." *Anaesthesia* (2020).

Wiese, Andrew D., and Carlos G. Grijalva. "The use of prescribed opioid analgesics & the risk of serious infections." (2018): 849-852.

Liang, X., Liu, R., Chen, C., Ji, F., and Li, T. "Opioid System Modulates the Immune Function: A Review." Transl Perioper Pain Med. 2016; 1(1): 5-13.

Simon Haroutounian. "Postoperative opioids, endocrine changes, and immunosuppression." Pain Reports. 3 (2018) e640.

Toby K. Eisenstein. "The Role of Opioid Receptors in Immune System Function." Frontiers in Immunology. 2019:(10) 2904.

Effective Management of Acute Pain Recommendations from the Ad Hoc Committee on Pain Management and Prescription Drug Abuse. South Dakota State Medical Association. Draft date: 06/01/2019.

Pino, C. A., Covington, M., and Wakeman, S. E. Prescription of opioids for acute pain in opioid naïve patients.

The invention claimed is:

1. A single formulation consisting of:
   a. acetaminophen;
   b. one or more nonsteroidal anti-inflammatory drug;
   c. a gabapentinoid; and
   d. at least two additional active ingredients selected from the group consisting of:
      alpha 2 agonists, corticosteroids, H2 blockers, proton pump inhibitors, antacids, SSRIs (Selective Serotonin Reuptake Inhibitors), SNRIs (Serotonin Norepinephrine Reuptake Inhibitors), sleep aids drugs, natural sleep aids, magnesium, zinc, vitamin C, vitamin D, and tramadol.

2. The single formulation of claim 1, wherein the at least two additional active ingredients further comprises one or more of anti-convulsants and anti-seizure medications.

3. The single formulation of claim 1, wherein the single formulation further comprises one or more excipients.

4. The single formulation of claim 1, wherein the single formulation comprises 500 mg of acetaminophen, 50 mg of a nonsteroidal anti-inflammatory drug, 50 mg of gabapentinoid, and two or more active ingredients.

5. The single formulation of claim 1, wherein the single formulation comprises 650 mg of acetaminophen, 100 mg of a nonsteroidal anti-inflammatory drug, 75 mg of a gabapentinoid, and two or more active ingredients.

6. The single formulation of claim 1, wherein the single formulation comprises 1000 mg of acetaminophen, 100 mg of a nonsteroidal anti-inflammatory drug, 75 mg of gabapentinoid, and two or more active ingredients.

7. The single formulation of claim 1, wherein the single formulation comprises 1000 mg of acetaminophen, 200 mg of a nonsteroidal anti-inflammatory drug, 75 mg of gabapentinoid, and two or more active ingredients.

8. The single formulation of claim 1, wherein the single formulation is given to a patient on the first day every four hours.

9. A method of treating pain, consisting of administering the single formulation of claim 1.

10. The method of claim 9, wherein the single formulation comprises 500 mg of acetaminophen, 50 mg of a nonsteroidal anti-inflammatory drug, 50 mg of a gabapentinoid, and two or more active ingredients.

11. The method of claim 9, wherein the single formulation comprises 650 mg of acetaminophen, 100 mg of a nonsteroidal anti-inflammatory drug, 75 mg of a gabapentinoid, and two or more active ingredients.

12. The method of claim 9, wherein the non-steroidal anti-inflammatory drug is a COX-2 selective nonsteroidal anti-inflammatory drug.

13. The method of claim 9, wherein the gabapentinoid is gabapentin.

14. The method of claim 9, wherein the single formulation is used to treat a patient to manage pain associated with a COVID-19 infection.

15. The method of claim 9, wherein the single formulation is used to treat a patient to manage pain, wherein the patient is also infected with COVID-19.

16. An inhaler to dispense the single formulation according to claim 1.

17. A single formulation consisting of:
a. acetaminophen;
b. one or more nonsteroidal anti-inflammatory drug;
c. a gabapentinoid; and
d. at least two additional active ingredients selected from the group consisting of:
alpha 2 agonists, corticosteroids, H2 blockers, proton pump inhibitors, antacids, SSRIs (Selective Serotonin Reuptake Inhibitors), SNRIs (Serotonin Norepinephrine Reuptake Inhibitors), sleep aids drugs, natural sleep aids, magnesium, and tramadol, zinc, vitamin C, vitamin D, and tramadol,
and
wherein the single formulation is given to a patient on the first day every eight hours.

18. A single formulation consisting of:
a. acetaminophen;
b. one or more nonsteroidal anti-inflammatory drug;
c. a gabapentinoid; and
d. at least two additional active ingredients selected from the group consisting of:
alpha 2 agonists, corticosteroids, H2 blockers, proton pump inhibitors, antacids, SSRIs (Selective Serotonin Reuptake Inhibitors), SNRIs (Serotonin Norepinephrine Reuptake Inhibitors), sleep aids drugs, natural sleep aids, magnesium, zinc, vitamin C, vitamin D, and tramadol,
and
wherein the single formulation is dispensed by an inhaler to a patient.

19. A single formulation consisting of:
a. acetaminophen;
b. one or more nonsteroidal anti-inflammatory drug;
c. a gabapentinoid;
d. one or more corticosteroids; and
e. one or more H2 blockers.

20. A single formulation consisting of:
a. acetaminophen;
b. one or more nonsteroidal anti-inflammatory drug;
c. a gabapentinoid; and
d. at least two additional active ingredients selected from the group consisting of:
corticosteroids, H2 blockers, magnesium, zinc, vitamin C, and vitamin D.

* * * * *